United States Patent [19]

Leighton

[11] Patent Number: 4,553,533
[45] Date of Patent: Nov. 19, 1985

[54] INTRA-URETHRAL PROSTHETIC SPHINCTER VALVE

[76] Inventor: Stephen B. Leighton, 93 Jefferson Ave., Maplewood, N.J. 07040

[21] Appl. No.: 550,040

[22] Filed: Nov. 8, 1983

[51] Int. Cl.⁴ .............................................. A61F 1/00
[52] U.S. Cl. .................................... 128/1 R; 623/14; 128/325
[58] Field of Search ............... 128/DIG. 25, 344, 1 R; 604/335, 256, 34, 247; 3/1

[56] References Cited

U.S. PATENT DOCUMENTS

| | | | |
|---|---|---|---|
| 2,638,093 | 5/1953 | Kulick | 128/133 |
| 3,372,695 | 3/1968 | Beliveau et al. | 128/1 |
| 3,797,478 | 3/1974 | Walsh et al. | 604/256 |
| 3,903,894 | 9/1975 | Rosen et al. | 128/346 |
| 4,167,952 | 9/1979 | Reinicke | 128/1 R |
| 4,209,010 | 6/1980 | Ward et al. | 128/1 R |
| 4,222,377 | 9/1980 | Burton | 128/1 R |
| 4,256,093 | 3/1981 | Helms et al. | 128/1 R |
| 4,386,601 | 6/1983 | Trick | 128/1 R |

FOREIGN PATENT DOCUMENTS

526357  9/1976  U.S.S.R. ..................... 128/DIG. 25

Primary Examiner—Michael H. Thaler

[57] ABSTRACT

A prosthetic urethral sphincter valve that is placed totally within a patient's urethra, the valve including a collapsible flexible thin-walled annular bag member secured in a rigid casing with flexible retaining petals at its top end receivable in the patient's bladder. An upstanding annular flexible thin-walled diaphragm is provided over an inturned top flange on the casing, the flange having small flow apertures forming damping ports communicating with the flexible bag member. The bottom end of the bag member is engaged with an annular guide urged upwardly by a coiled spring bearing on an inturned bottom flange of the casing. The working space between the bag member and the diaphragm is filled with viscous grease. The bag member has a central tubular passage which is normally occluded or kinked by the upward biasing force of the coiled spring. When the patient exerts sustained bladder pressure, the flexible bag member is distended downwardly, causing the central tubular passage to elongate and thereby open up, enabling it to pass urine. After urination, the bladder pressure is released, allowing the spring to return the bag member to its collapsed state and restore the occlusion of its central tubular passage, providing positive shut-off of the valve.

12 Claims, 3 Drawing Figures

INTRA-URETHRAL PROSTHETIC SPHINCTER VALVE

FIELD OF THE INVENTION

This invention relates to prosthetic urethral valves for controlling urinary continence, and more particularly to a prosthetic urethral valve which is installed totally within a patient's urethra without surgery, and which is controlled by the patient's voluntary elevation of bladder pressure substantially in a normal manner.

BACKGROUND OF THE INVENTION

Prosthetic urethral valves of the prior art for incontinent patients involve numerous disadvantages. Most urethral valves of the prior art involve an inflatable cuff around the outside of the urethra, or a catheter that extends beyond the distal end of the urethra. The former type of urethral valve requires surgery for installation, and the latter type is non-cosmetic and invites infection. Also, most of the previously proposed urethral valve devices must be operated externally and depend on manual intervention.

Therefore, there is a definite need for a non-surgically installed prosthetic urethral valve which has functional sensitivity to the natural physiological sustained internal bladder pressure produced voluntarily by the patient, rather than by external manual control.

A preliminary search of the prior U.S. patents relating to this art revealed the following U.S. prior patents of interest all of which suffer the aforementioned defects:

Kulick, 2,638,093;
Beliveau, 3,372,695;
Rosen et al, 3,903,894;
Reinicke, 4,167,952;
Ward et al, 4,209,010;
Burton, 4,222,377;
Helms et al, 4,256,903;
Trick, 4,386,601.

SUMMARY OF THE INVENTION

The prosthetic urethral valve of the present invention is placed totally within the urethra, without surgery, and operates with close simulation of natural physiologic function, namely, by naturally produced sustained elevation of the patient's bladder pressure. Momentary elevation of bladder pressure due to coughing, jumping, etc., does not persist long enough to open the valve. However, voluntary elevation of bladder pressure, for example, for 10-20 seconds by the patient's execution of "straining" procedure, exerts pressure on a pressure-sensitive diaphragm portion of the device, which is transmitted to a distensible valve element via a viscous liquid medium. The transmitted pressure changes the shape of the distensible valve element sufficiently to change it from a sealed "kinked" configuration to a configuration defining a tubular channel, against the force of a biasing means which normally maintains the sealed configuration.

Accordingly, an object of the invention is to overcome deficiencies in the prior art, such as mentioned above.

Another object is to provide for improved artificial sphincter control.

Yet another object of the invention is to provide a novel and improved prosthetic urethral valve which overcomes the disadvantages and deficiencies of previously known devices for controlling a patient's urinary continency.

A further object of the invention is to provide a novel and improved urethral valve which can be installed totally within the urethra of a patient without surgery.

A still further object of the invention is to provide an improved urethral valve which closely simulates natural physiologic function.

A still further object of the invention is to provide an improved prosthetic urethral valve which opens in response to substantially normal voluntary elevation of the bladder pressure of a patient but which does not open responsive to momentary natural elevation of bladder pressure due to coughing, jumping, or the like.

A still further object of the invention is to provide an improved prosthetic urethral valve which can be totally installed in the patient's urethra without requiring surgery, which is cosmetically normal, which minimizes the risk of infection, which provides normal, substantially positive sealing action, which opens responsive to sustained elevation of bladder pressure, and which slowly returns to a closed state after release of bladder pressure.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
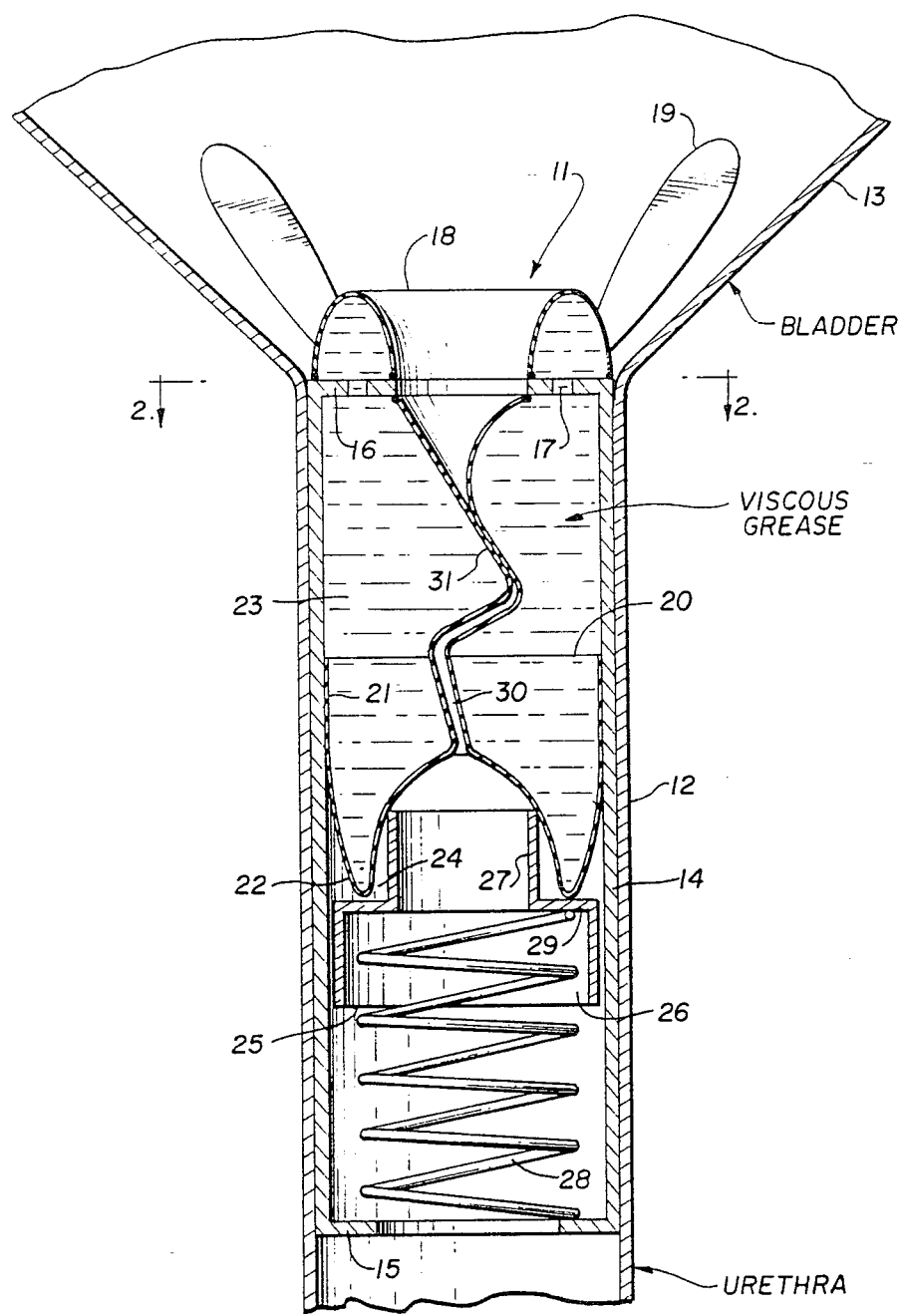
FIG. 1 is an enlarged schematic vertical cross-sectional view taken axially through a prosthetic urethral valve according to the present invention, shown installed in the upper end portion of a patient's urethra, and shown in its normal sealing configuration.
Figure 2:
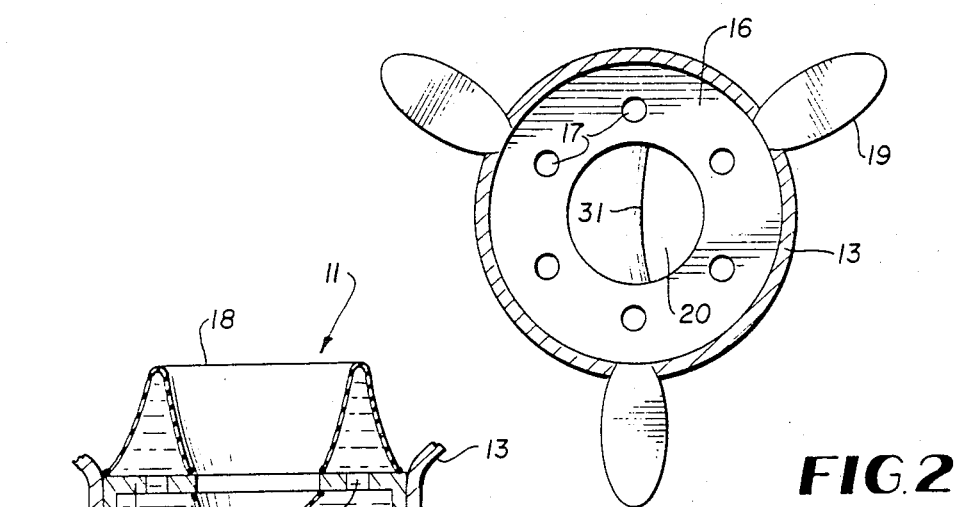
FIG. 2 is a horizontal cross-sectional view taken substantially on line 2—2 of FIG. 1.

Referring to the drawings, 11 generally designates an improved prosthetic urethral valve assembly according to the present invention, shown installed in the upper end portion of a patient's urethra 12 and extending into the patient's bladder 13. The valve assembly 11 comprises a rigid cylindrical casing 14 desirably of stainless steel or plastic which is both biocompatible and will not corrode or degrade in a urine environment, and having an inturned annular bottom flange 15 and an inturned annular top flange 16 formed with a plurality of equally angularly spaced, relatively small, flow apertures 17. An upstanding diaphragm member 18 of annular configuration, formed of thin flexible sheet material, such as thin plastic or rubber (e.g. silicone or polyurethane) sheet material, is sealingly continuously secured at its outer peripheral edge to the outer corner rim of annular top flange 16 and at its inner peripheral edge to the inner rim of flange 16, defining an annular diaphragm chamber of substantial nomally-expanded volume. The smaller the holes 17, the less likely is it that the film 18 can balloon therethrough.

A plurality of evenly angularly spaced resilient retaining petal members 19 are fixedly secured to the outer corner rim of annular top flange 16 in outwardly and upwardly divergent relationship to the top of casing 14 and are flatly retentively engageable with the upwardly divergent bottom wall surface of the bladder 13 to hold the prosthetic sphincter valve assembly 11 in the working position thereof illustrated in FIG. 1. The resilient petal members 19 are sufficiently flexible to be squeezed inwardly enough to permit insertion of the valve device 11 into the urethra 12 and to allow it to be pushed upwardly in the urethra to its working position. Inflatable balloons may be used in place of the petal members 19.

A generally annular distensible bag member 20 of flexible thin sheet material, preferably silicone resin or polyurethane, is fixedly continuously secured at its marginal peripheral portion 21 to the inside surface of rigid casing 14 at a location spaced substantially below top flange 16, and is fixedly continuously secured at its top inner peripheral rim to the inner rim of annular flange 16, to define a downwardly distensible chamber with an annular bottom thrust portion 22. The annular bag member 20 may be formed of a flexible tube of diameter about $\frac{1}{2}$ the diameter of the cylindrical casing 14 and length about $1\frac{1}{3}$ the distance between the flange 16 and the resting position of a thrust collar 27, described below. The annular thrust portion 22 at the bottom of the flexible tube may comprise a disk shaped film connected at its outer edge to the interior of the casing 14 and at its inner edge to the bottom of the flexible tube.

Such distensible chamber 20 is in communication with the upstanding diaphragm chamber 18 via the small flow apertures 17. Diaphragm chamber 18 and the downwardly distensible chamber defined by bag member 20 and the upper wall portion of casing 14 are filled with relatively viscous liquid, grease or gel 23, such as viscous silicone grease.

The annular bottom thrust portion 22 is engaged in an annular seat 24 defined between an annular guide plunger 25 and the inside wall surface of casing 14. The plunger 25 comprises a large annular bottom chamber 26, slidably disposed in casing 14, formed with a reduced upstanding annular thrust collar 27 coaxial with bottom chamber 26 and defining the seat 24. A linear or non-linear biasing means such as a coiled stainless steel spring 28 or an elastomeric tube or the like bears between bottom flange 15 and the annular shoulder 29 defined by the reduced thrust collar 27.

Spring 28 normally provides enough upward force to cause the flexible tube of the bag member 20 to deform or "kink" so as to occlude its central channel, shown at 30, by forming a seal or occlusion, shown, for example, at 31. This is the normal closed state of the prosthetic valve device 11, and is illustrated in FIG. 1. Under these conditions the diaphragm chamber 18 attains its maximum volume. Bladder pressure rises gradually as the bladder 13 fills, but will not normally cause sufficient distension of the bag member 20 to open up the channel 30. Also, momentary elevation of bladder pressure due to coughing, jumping, spasmodic bladder contraction, or the like, will not open the channel 30, due to the damping action provided by the restricted flow apertures 17. The diaphragm 18 cooperates with the apertures and the viscous liquid to balance pressure, prevent premature opening of the valve and ensure that the kinked tube forming the occluded central channel does not open until near the end of downward movement of the thrust collar 27.

Figure 3:
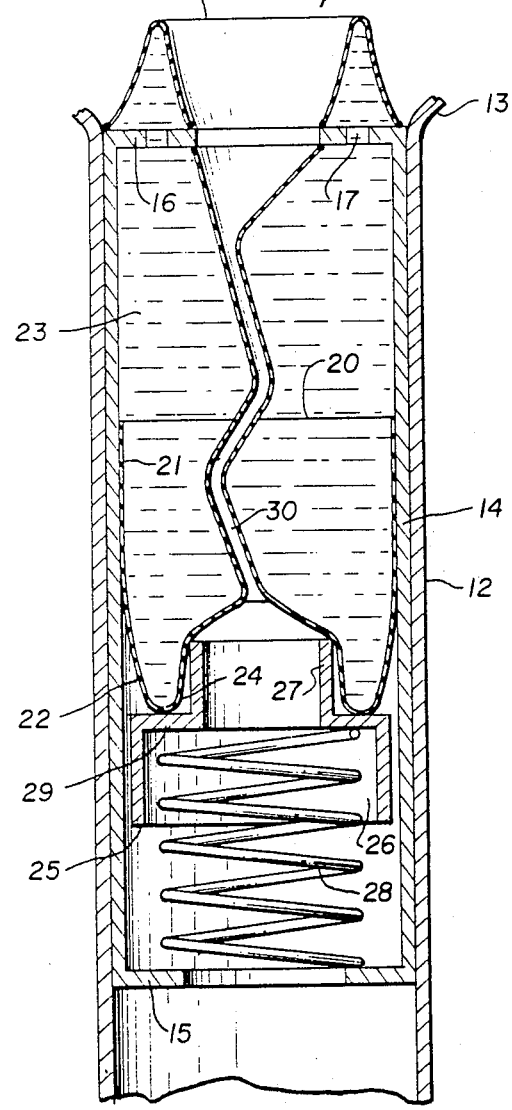
FIG. 3 is a vertical cross-sectional view similar to FIG. 1 but showing the valve in an open state responsive to the patient's sustained elevation of bladder pressure.

The patient may raise the bladder pressure voluntarily and sustain it for a substantial duration, sufficient to open the passage 30, by exerting intra-abdominal pressure by a "Valsalva" maneuver (such as in straining at stool), or by action somewhat similar to normal urination. The voluntary sustained elevation of bladder pressure for example for 10–20 seconds, causes the viscous liquid 23 to be forced out of the annular diaphragm 18 via the small apertures 17 and causes the annular diaphragm 18 to assume a lessened-volume configuration, as shown in FIG. 3, the ejected liquid 23 pushing downward through the bag member 20 against the force of spring 28, and causing downward distension of the bag member. This acts to lengthen the flexible tube of the bag member sufficiently to open up the occlusion 31 and clear the flow channel 30, whereby substantially normal urinary drainage from bladder 13 can be accomplished. Release of bladder pressure allows the spring 28 to expand so as to restore the normal closed state of the valve assembly, shown in FIG. 1.

FIG. 3 shows the downwardly-distended state of the bag member 20 produced by the voluntary sustained elevation of bladder pressure above described, which transfers the liquid 23 from the annular diaphragm 18 to the bag member 20 via the apertures 17 and which overcomes the upward biasing force of spring 28 to allow the downward distension of said bag member.

While a specific embodiment of an improved prosthetic urethral valve device has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

For example, the invention can take substantially different forms than the embodiment disclosed above, it being understood that the device requires only a suitable slow friction means such as a damping element, a suitable biasing means such as a spring, both of which move in response to bladder pressure, and a threshold detection means that has no output until the friction means and biasing means have moved a certain distance, whereupon the threshold detection means opens a suitable valve to permit passage of the urine. While in the illustrated embodiment the grease moving through the orifice constitutes the viscous friction means and the spring constitutes the biasing means (elastomeric walls could be substituted for the spring) and the kinked tube performs the function of both the threshold detector and the valve, it will be very clear that other means could be substituted, e.g. an electrically controlled valve could be used controlled by a threshold detection means including an electrical switch which closes upon a predetermined movement of the viscous friction means and the biasing means.

Other embodiments also will be able to be designed in view of the disclosure above, using the principle of a low pass filter insensitive to pressure spikes, but sensitive to steady pressure. Thus, another embodiment involves a sliding spool valve and a system of bellows, springs and orifices to detect and react to a given degree of intra-abdominal pressure over a sufficient period of time. Another embodiment involves a rolling (everting) tube with variable cross-section and a ball in the center.

What is claimed is:

1. A prosthetic urethral sphincter valve comprising a rigid tubular casing adapted to be placed in a patient's urethra with its top end portion located adjacent and exposed to the patient's bladder, inturned annular flange means on the top end portion of said casing, said flange means being provided with flow-damping aperture means, annular upstanding thin-walled flexible diaphragm means secured peripherally on said flange means and overlying said aperture means, substantially annular thin-walled flexible bag means connected between the inner peripheral edge portion of said flange means and the inside peripheral wall surface of said casing and having a depending annular thrust portion and inner wall means defining a substantially tubular central through passage, viscous liquid material substantially filling the bag means and said flexible diaphragm means, and upward biasing means in the rigid casing drivingly engaging said depending annular thrust portion to normally urge the bag means to assume a collapsed state wherein said tubular central passage is occluded, said bag means being downwardly extensible to open said tubular central through passage responsive to sustained bladder pressure acting externally on said flexible diaphragm means.

2. The prosthetic valve of claim 1, and outwardly biased resilient retaining petal means on the top end portion of said casing retentively engageable in the patient's bladder.

3. The prosthetic valve of claim 2, and wherein said retaining petal means comprises a plurality of resilient petal elements secured to the top rim portion of said casing and being biased to diverge upwardly and outwardly from said top rim portion.

4. The prosthetic valve of claim 1, and wherein the upward biasing means comprises an annular guide member having an annular seat receiving said depending annular thrust portion, and spring means mounted in the casing and bearing upwardly on said guide member.

5. The prosthetic valve of claim 4, and wherein the casing has an inturned bottom annular flange and wherein said spring means bears between said bottom annular flange and said annular guide member.

6. The prosthetic valve of claim 1, and wherein said flowdamping aperture means comprises a plurality of relatively small apertures formed in the flange means and being angularly spaced around the central axis of the casing.

7. The prosthetic valve of claim 1, and wherein the liquid material filling the bag means and the flexible diaphragm means comprises viscous grease material.

8. The prosthetic valve of claim 1, and wherein said upward biasing means comprises an annular guide member slidably mounted in the casing, said guide member comprising a large annular bottom chamber formed coaxially with a reduced upstanding thrust collar externally defining an annular seat receiving said depending annular thrust portion of the bag means, and spring means mounted in the casing below said guide member and bearing upwardly in said large annular bottom chamber.

9. The prosthetic valve of claim 8, and wherein said casing has an inturned bottom flange and said spring means bears between said inturned bottom flange and said large annular bottom chamber.

10. The prosthetic valve of claim 1, and wherein said upstanding annular diaphragm means is secured at its inner periphery to the inner peripheral edge of said inturned annular flange means and is secured at its outer periphery to the peripheral outer rim portion of the rigid casing.

11. A prosthetic urethral sphincter valve for implantation within the urethra adjacent the bladder, and capable of control by the exertion by the patient of sustained intra-abdominal pressure for at least several seconds, said valve comprising tubular casing means for said valve, said casing means being adapted to be placed in a patient's urethra with its top end portion located adjacent and exposed to the patient's bladder;

holding means on the top end portion of said casing for holding said casing in place within the patient's urethra;

valve means for maintaining said urethra in a normally closed condition;

damping means for transmitting sustained intra-abdominal pressure from the patient to the valve means, whereby sustained intra-abdominal pressure from the patient causes movement of said damping means from an initial at rest position to a threshold detection position;

biasing means for biasing and returning said damping means to said initial position;

threshold detection means for detecting when said damping means has reached said threshold position; and wherein the valve means opens to permit passage of urine therethrough upon actuation by said threshold detection means upon said damping means reaching said threshold position, said valve closing as said biasing means moves said damping means away from said threshold position.

12. A prosthetic urethral sphincter valve according to claim 11, wherein said damping means comprises a flow-damping restricted aperture means, annular upstanding thin-walled flexible diaphragm means secured on said tubular casing above said flow damping aperture means and a quantity of a viscous liquid within said diaphragm;

said valve means comprises a substantially annular thin-walled flexible bag means connected to the interior of said tubular casing, and a quantity of said viscous liquid, retained within said substantially annular thin-walled flexible bag means, with at least a portion of said viscous liquid being able to move between said diaphragm means and said bag means through said flow-damping aperture means; and said threshold detector means and said valve together comprise a kinked tube which forms the inner annular surface of said substantially annular thin-walled flexible bag means.

* * * * *